US009127239B2

(12) United States Patent
Garner

(10) Patent No.: US 9,127,239 B2
(45) Date of Patent: Sep. 8, 2015

(54) CLEANING, SANITISING AND STERILISING PREPARATIONS

(75) Inventor: George V. Garner, Greater Manchester (GB)

(73) Assignee: Arcis Biotechnology Holdings Limited, Warrington (GB)

( * ) Notice: Subject to any disclaimer, the term of this patent is extended or adjusted under 35 U.S.C. 154(b) by 33 days.

(21) Appl. No.: 12/866,948

(22) PCT Filed: Mar. 12, 2009

(86) PCT No.: PCT/US2009/036900
§ 371 (c)(1),
(2), (4) Date: Aug. 10, 2010

(87) PCT Pub. No.: WO2009/117299
PCT Pub. Date: Sep. 24, 2009

(65) Prior Publication Data
US 2010/0323895 A1   Dec. 23, 2010

(30) Foreign Application Priority Data

Mar. 16, 2008 (IL) .......................................... 190181

(51) Int. Cl.
A01N 47/44 (2006.01)
A01P 1/00 (2006.01)
A01P 3/00 (2006.01)
A01P 13/00 (2006.01)
C11D 3/48 (2006.01)
C11D 1/66 (2006.01)
C11D 1/835 (2006.01)
C11D 3/32 (2006.01)

(52) U.S. Cl.
CPC *C11D 3/48* (2013.01); *A01N 47/44* (2013.01); *C11D 1/66* (2013.01); *C11D 1/835* (2013.01); *C11D 3/323* (2013.01)

(58) Field of Classification Search
None
See application file for complete search history.

(56) References Cited

U.S. PATENT DOCUMENTS

| 4,748,158 | A | | 5/1988 | Biermann et al. |
| 4,920,100 | A | | 4/1990 | Lehmann et al. |
| 5,529,713 | A | * | 6/1996 | Gauthier-Fournier ........ 510/384 |
| 5,856,290 | A | | 1/1999 | van Buskirk et al. |
| 6,303,557 | B1 | | 10/2001 | Colclough |
| 6,656,919 | B1 | | 12/2003 | Baugh et al. |
| 6,730,654 | B2 | | 5/2004 | Godfroid et al. |
| 6,814,088 | B2 | | 11/2004 | Barnabas et al. |
| 6,838,425 | B2 | * | 1/2005 | Ghosh et al. ................... 510/392 |
| 7,082,951 | B2 | | 8/2006 | Barnabas et al. |
| 7,094,741 | B2 | | 8/2006 | Barnabas et al. |
| 7,166,563 | B2 | | 1/2007 | Woodhead |
| 2003/0099570 | A1 | | 5/2003 | Barnabas et al. |
| 2004/0013638 | A1 | * | 1/2004 | Aubay et al. ................ 424/78.37 |
| 2004/0248760 | A1 | | 12/2004 | Woodhead |
| 2006/0166849 | A1 | | 7/2006 | Kilkenny et al. |

FOREIGN PATENT DOCUMENTS

| EP | 0000224 A1 | 10/1979 | |
| EP | 0185971 A1 | 7/1986 | |
| EP | 0987321 A2 | 3/2000 | |
| GB | 321729 * | 11/1929 | ................ D06L 1/12 |
| JP | S579717 A | 1/1982 | |
| RU | 94041329 A * | 10/1996 | ........... C09D 127/08 |
| WO | 9820738 A1 | 5/1998 | |
| WO | 0135743 A1 | 5/2001 | |
| WO | 2007101445 | 9/2007 | |

OTHER PUBLICATIONS

"The antiseptic properties of sodium fluoride." American Druggist, 1891, v. 20, William Wood & Company, p. 89.*
Patent Cooperation Treaty, International Search Report for PCT/US2009/036900 dated Sep. 30, 2009, 5 pages.
Patent Cooperation Treaty, Written Opinion of the International Searching Authority for PCT/US2009/036900 dated Sep. 30, 2009, 7 pages.
European Patent Office, Supplementary European Search Report for Application EP09721686 dated Jul. 17, 2014, 7 pages.

* cited by examiner

*Primary Examiner* — Mina Haghighatian
*Assistant Examiner* — Erin Hirt
(74) *Attorney, Agent, or Firm* — Hoffman Warnick LLC

(57) ABSTRACT

The present invention relates to a cleaning preparation, namely to a cleaning, disinfecting, sanitizing and sterilizing preparation. Said preparation comprises a mixture of cationic microbiocides and non-ionic surfactants.

7 Claims, No Drawings

CLEANING, SANITISING AND STERILISING PREPARATIONS

CROSS-REFERENCE TO RELATED APPLICATIONS

This application is filed under the provisions of 35 U.S.C. §371 and claims the priority of International Patent Application No. PCT/US2009/036900 filed on Mar. 12, 2009, which in turn claims priority of Israeli Patent Application No. IL 190, 181 filed on Mar. 16, 2008, the contents of which are incorporated by reference herein for all purposes.

TECHNICAL FIELD OF THE INVENTION

The present invention relates to enhancement and optimisation in cleaning, sanitising and sterilising preparations. More particularly the present invention relates to preparations formulated for the disinfection and sterilisation of materials, commodities and surfaces contaminated with one or more species of micro-organisms including bacteria (and mycobacteria), fungi, algae and yeasts and their associated spores. The invention provides preparations whereby it is not only a sterilising preparation for killing and rendering spores lifeless but it also affects the necromass so formed that it becomes easily removable by water rinsing hence reducing the likelihood of biofilm formation.

Therefore the present invention gives a solution for the requirement of effective preparations that can be used for the cleaning, sanitisation and sterilisation in general and more particularly cleaning, sanitisation and sterilisation of surfaces and equipment in the human and animal healthcare sector as part of an holistic infection control strategy.

BACKGROUND OF THE INVENTION

There are known cleaning techniques that involve high temperatures that may be detrimental to the particular equipment or that involve powerful chemical reagents such as oxidants like peracetic acid that also adversely affect not only the primary medical devices but also the equipment used to clean the devices.

It is well known that transient supramolecular organisation of amphoteric molecules form micelles. The transitional quality of such organized groups is believed to provide an explanation of the enhanced activity of microbiocides when combined in certain cleaning preparations as reported in literature.

There is a known detergent action, namely the gathering together of surfactant molecules to form micelles. Such micelles are also alluded to in known theories explaining the observed biological action of cationic biocides such as quaternary ammonium compounds. Molecules of this type interact fleetingly with the phospholipids and peptidoglycan parts of cytoplasmic membranes of micro-organisms, which interaction causes these membranes to become disturbed and then to explode, leading to the death of the cell.

Up to the present time, an overabundance of inventions for preparations for disinfecting and sterilising materials and surfaces contaminated with bacteria and bacterial spores have come about through empirical observations of biological action.

All of these inventions require some form of microbiocidal fluid which is brought into contact with the contaminated material or surface long enough to be able to disinfect and sterilise said contaminated material or surface.

Prior Art provides several cleaning preparations as follows:

Baugh et al. U.S. Pat. No. 6,656,919 describes a microbiocidal solution which can range from a simple solution of a single component such as aqueous formaldehyde to complex mixtures of microbiocides and various adjuncts including microbiologically active components such as germination promoters or other inert material that displays surfactant properties. The microbiocidal properties of cationic surfactants such as quaternary ammonium compounds (QAC) and biguanidinium salts are well known and authenticated.

Spooner et al WO9820738 describes microbiological activity which was found to be enhanced when bis(biguanide) microbiocides were combined with polymeric biguanides in contact lens cleaning solutions.

Van Buskirk et al U.S. Pat. No. 5,856,290 describes the combination of QAC and N-alkylpropylenediamine microbiocides with a mixture of non-ionic surfactants which was observed to lead to a noticeable improvement in microbiocidal efficacy.

Lehman et al U.S. Pat. No. 4,920,100 describes bactericidal alcohols and carboxylic acids which were also observed to demonstrate potentiated effects when mixed with certain non-ionic surfactants.

Biermann et al U.S. Pat. No. 4,748,158 describes potentiation in dental cleaning applications of mixtures of chlorhexidine salts and alkylpolyglucosides.

Toshuki et al JP57009717 describes synergistic germicidal activity in mixtures of chlorhexidine salts or polyhexamethylenebiguanide and polyoxyethylene alkyl ethers in the proportions 1:1:W3 which has been reported.

EP05252443.6 suggests the formation of a transient intermediate to explain the observed improvement in minimum inhibitory concentration data for chlorhexidine salts when mixed with various non-ionic surfactants, and until that time a mechanism explaining the origin of such improved microbiocidal efficacy had not been defined.

U.S. Pat. No. 6,303,557 uses biocides and surfactants which differ from those of the present invention, does not include the aliphatic alcohol and requires the presence of sequesterants and amphoteric surfactants to achieve its enhanced microbiocidal activity.

Moreover, there are known U.S. Pat. Nos. 6,814,088, 7,082,951 and 7,094,741 which are for aqueous compositions for treating a surface. However said patents are for preparations which afford superior filming/streaking and shine retention whilst providing disinfecting/antimicrobial benefits. The preparations/compositions of said patents are different from that of the present invention inter alia in that they exclude the component QAC (Quaternary Ammonium Compound), being a cationic microbiocide, which is an essential component of the present invention.

Another known U.S. Patent is U.S. Pat. No. 7,166,563. Said patent is different from the present application as it differs in that QAC are absent from the mixture which may contain PHMB and APG together with other components not used in the present invention.

As noted from the above, none of the above Prior Art gives a solution for the most efficient cleaning, sanitising and sterilising preparations.

It has been observed in some formulations that the activity of particular microbiocides is compromised and considerably diminished by the presence of certain surfactants. It is the recognition of such behaviour by means of empirical observation and the subsequent development of an explanatory theorem which has brought about the formulation of the present invention.

SUMMARY OF INVENTION

According to the present invention, cleaning, sanitising and sterilising preparations (hereinafter "cleaning preparation") may be prepared using known microbiocides provided that they are mixed in such a way that chemical species that interfere with said preparation are avoided and/or destroyed. The present invention thus consists in a cleaning preparation comprising a mixture of cationic microbiocides and non-ionic surfactants in an aqueous matrix.

DETAILED DESCRIPTION OF THE INVENTION

The present invention consists in a cleaning preparation comprising a mixture of cationic microbiocides and non-ionic surfactants in a ratio of between 8:1 to 2:1 in an aqueous matrix.

For clarity's sake it should be noted that when referring to cleaning, sanitisation and sterilisation preparations it refers to cleaning, sanitisation and sterilisation preparations per se or to any other preparations from said group such as disinfecting preparations, preparations for use in hygiene (disinfecting), preparations for use in hygiene (sterilising), disinfectants, anti-bacterial preparations, anti-bacterial preparations for medical use, detergents for medical use, detergents for medical use having anti-bacterial properties, disinfectants for hygiene purposes, disinfectants for medical and veterinary use, disinfectants for hygiene purposes or for medical and veterinary use having anti-bacterial properties, Bactericidal preparations, Virucdidal preparations, Fungicidal preparations, Tuberculocidal preparations, Sproicidal preparations, Biocides, anti-microbial preparations, chemicals having anti-microbial properties (medical or veterinary), cleaning and sanitising solutions and preparations for medical use, rinse and drying aids for use in medical washing applications, chemicals for use in cleansing, disinfecting and/or decontamination applications in the medical field, medical scrubs (sterilising or disinfecting, scrubs (preparations) for medical use, surface hygiene products, medicated anti-bacterial washes, anti-bacterial cleansers In one embodiment of the present invention, the cleaning preparation comprises a mixture of cationic microbiocides and non-ionic surfactants in a ratio of between 7:1 to 2:1 and more preferably 2.3 to 1 in an aqueous matrix.

In another embodiment of the present invention, the cleaning preparation comprises a mixture of cationic microbiocides and non-ionic surfactants in a ratio of between 8:1 to 4:1.

In a further embodiment of the present invention, the mixture of cationic microbiocides and non-ionic surfactants forms transient supramolecular assemblies which enhance the microbiocidal efficiency.

According to the present invention, cleaning, sanitising and sterilising solutions can be prepared using known microbiocides provided that they are mixed in such a way that transient supramolecular assemblies can be formed and that chemical species which interfere with this molecular organisation can be avoided.

The cationic microbiocides of the present invention may be selected from among (a) guanidine salts and (b) positive non-metallic salts, preferably quaternary ammonium salts.

The guanidine salts of the present invention may be guanidine salts per se, biguanidinium salts, guanide salts, biguanidine salts or biguanide salts, and all the above are standing for the same molecules.

The guanidine salts of the present invention may be selected from among the following salts, however they are not restricted thereto: chlorhexidine digluconate, dihydrochloride and diacetate; hexamethylenebis(ethylhexyl)biguanide dihydrochloride; oxocyclohexadienylideneaminoguanidine thiosemicarbazone; bis(chlorophenylamidino)piperazinedicarboxamidine dihydrochloride and polyhexamethylenebiguanidine hydrochloride.

The positive non-metallic salts may be selected from among quaternary ammonium salts, phosphonium salts and sulfonium salts.

The quaternary ammonium salts of the present invention may be selected from among the following salts, however they are not restricted thereto: quaternary salts containing either or both aliphatic or aromatic moieties; aliphatic groups including alkoxy groups which may contain from one to 30 carbon atoms in linear or branched arrangements; alicyclic groups which may be cyclohexyl and its alkylated and alkoxylated derivatives. The preferred quaternary ammonium salt of the present invention is didecyldimethylammonium chloride.

The counter ions of the guanidine and quaternary ammonium salts may be selected from among halides, preferably chloride; bicarbonate, borate, carbonate, fluoborate, fluoride, phosphate, and sulphate.

In a preferred embodiment of the present invention, the cationic microbiocides of the present invention consist of a mixture of polymeric biguanidinnium chloride or polyhexamethylenebiguanidine hydrochloride and didecyldimethylammonium chloride in the ratio of between 1:1 and 1:1.25.

The non-ionic surfactants, i.e. the water soluble non-ionic surfactants of the present invention, are widely available and include primary and secondary alcohol ethoxylates and condensates with oligoglycosides; e.g. alkanol containing about 8 to 18 carbon atoms in either straight chain or branched arrangements condensed with six to ten moles of ethylene oxide or four to six moles of monosaccharide such as glucose.

In a preferred embodiment of the present invention, the non-ionic surfactants comprise an alkylpolyglucoside and an alkylethoxylate, most preferably a $C_9$-$C_{10}$alkyltetraglucoside, a $C_9$-$C_{11}$alkylhexaethoxylate or $C_{9-11}$ Alcoholethoxylate.

In a further embodiment of the present invention the cleaning preparation of the present invention comprises one or more solubilising agents. Such solubilising agents may include lower aliphatic alcohols such as ethanol, propan-1-ol and propan-2-ol; organic acids such as acetic acid, propanoic acid, glycolic acid, lactic acid and citric acid; and common salts of Group 1 & 2 metals such as potassium and sodium cations with any of the following anions: halides such as chloride, fluoride, bromide, iodide; phosphate, carbonate, bicarbonate, citrate, lactate, phosphate and sulphate; and combinations thereof. However they are not restricted to said agents.

In a preferred embodiment of the present invention, the solubilising agents comprise propan-2-ol, citric acid and optionally sodium fluoride. In one embodiment of the present invention the preparation of the present invention comprises at least 5% propan-2-ol, more preferably 10% and most preferably 20%. Preferably the preparation of the present invention comprises no more than 0.3% citric acid. In a further preferred embodiment of the present invention, the present invention comprises up to 30% propan-2-ol and comprises 0.4% citric acid.

In yet a further embodiment of the present invention, the cleaning preparation of the present invention comprises one or more further cationic surfactant such as alkylbenzyldimethylammonium chloride, Alkyl($C_{12-16}$) Dimethylbenzyl Ammonium Chloride and any other cationic surfactants, preferably with an aromatic moiety selected among but not restricted to benzylhexyldimethylammonium chloride, benzyloctyldimethylammonium chloride, benzyldecyldimethylammonium chloride, benzyldodecyldimethylammonium chloride, benzyltetradecyldimethylammonium chloride, benzyloctadecyldimethylammonium chloride, and similar species in which the benzyl moiety is replaced by tolyl- and xylyl- (ie methylbenzyl- and dimethylbenzyl-) moieties. In a further embodiment said cationic surfactant may be present at about one part per 8 parts of non-ionic surfactant mixture.

In yet a further embodiment said cationic surfactant may be present at about one part per 2.6 parts of non-ionic surfactant mixture. Said cationic surfactant may be used also as a clearing agent.

In a further option of the present invention the preparation comprises also fragrances, aromatics, coloring or any further materials. Such a material may be any commercial material such as: SAFA 30472 of Parfex S.A. in any desired amount such as 0.1 to 5%.

A preferred embodiment of the present invention comprises an aqueous preparation which may be diluted to form the required strength of the preparation comprising the following components: Propan-2-ol, Didecyldimethylammonium chloride, Polyhexamethylenebiguanidine HCld, Alkylpolyglucoside, Alkylbenzyldimethylammonium chloride, Alkylethoxylate, Citric acid and optionally Sodium fluoride.

In one embodiment of the present invention comprising the following components in an aqueous preparation in the following concentration shown in Table I (in order of decreasing abundance) expressed as weight percent:

TABLE I

| Component | from | to |
|---|---|---|
| Propan-2-ol | 0.16 | 30 |
| Didecyldimethylammonium chloride | 0.1 | 10 |
| Polyhexamethylenebiguanidine HCld | 0.08 | 9 |
| Alkylpolyglucoside | 0.04 | 4 |
| Alkylbenzyldimethylammonium chloride | 0.03 | 4 |
| Alkylethoxylate | 0.01 | 7 |
| Citric acid | 0.002 | 0.4 |
| Sodium fluoride | 0 | 0.1 |

In a further embodiment of the present invention comprising the following components in an aqueous preparation in the following concentration shown in Table II (in order of decreasing abundance) expressed as weight percent:

TABLE II

| Component | from | to |
|---|---|---|
| Propan-2-ol | 0.3 | 30 |
| Didecyldimethylammonium chloride | 0.1 | 10 |
| Polyhexamethylenebiguanidine HCld | 0.09 | 9 |
| Alkylpolyglucoside | 0.04 | 4 |
| Alkylbenzyldimethylammonium chloride | 0.04 | 4 |
| Alkylethoxylate | 0.07 | 7 |
| Citric acid | 0.004 | 0.4 |
| Sodium fluoride | 0 | 0.1 |

In a further embodiment of the present invention comprising the following components in an aqueous preparation in the following concentrations are shown in Table III (in order of decreasing abundance) expressed as weight percent:

TABLE III

| Component | from | to |
|---|---|---|
| Propan-2-ol | 0.16 | 16 |
| Didecyldimethylammonium chloride | 0.1 | 10 |
| Polyhexamethylenebiguanidine HCld | 0.08 | 8 |
| Alkylpolyglucoside | 0.04 | 4 |
| Alkylbenzyldimethylammonium chloride | 0.03 | 3 |
| Alkylethoxylate | 0.01 | 1 |
| Citric acid | 0.002 | 0.2 |
| Sodium fluoride | 0.001 | 0.1 |

In a further embodiment of the present invention, the preparation comprises an aqueous preparation in terms of weight per percent in the form of a concentrated solution having the following components: Propan-2-ol in the amount of 8.25; Didecyldimethylammonium chloride in the amount of 4.7; Polyhexamethylenebiguanidine HCld or polymeric biguanidinnium chloride in the amount of 4.33; Alkylpolyglucoside in the amount of 0.75; Alkylbenzyldimethylammonium chloride in the amount of 1.55; Alkylethoxylate in the amount of 3.25; Citric acid in the amount of 0.15 and Sodium fluoride in the amount of 0.001.

In another embodiment of the present invention, the preparation comprises an aqueous preparation in terms of weight per percent in the form of a super-concentrated solution having the following components: Propan-2-ol in the amount of 23; Didecyldimethylammonium chloride in the amount of 8.2; Polyhexamethylenebiguanidine HCld or polymeric biguanidinnium chloride in the amount of 7.1; Alkylpolyglucoside in the amount of 3.85; Alkylbenzyldimethylammonium chloride in the amount of 2.25; Alkylethoxylate in the amount of 1; and Citric acid in the amount of 0.4.

In a further embodiment of the present invention comprises a process for the manufacture of the cleaning preparation by combining the components at any ambient temperature.

In one embodiment of the present invention, the process for manufacture of the cleaning preparation comprises the following steps:

a. dissolve the salts in water (citric acid+sodium fluoride, if any)
b. add the Alkylethoxylate and Alkylpolyglucoside
c. add the Didecyldimethylammonium chloride and Alkylbenzyldimethylammonium chloride.
d. add Propan-2-ol
e. add Polyhexamethylenebiguanidine HCld In one embodiment, the cleaning preparation is manufactured by combining the following components as shown in Table IV in the order given at ambient temperature. Quantities are in parts by weight.

TABLE IV

| Ingredient | by wt | soln conc | weight percent |
|---|---|---|---|
| Didecyldimethylammonium chloride | 100 | as 50% solution | 10 |
| Alkylbenzyldimethylammonium Chloride | 30 | as 50% solution | 3 |
| Alkylpolyglucoside | 40 | as 75% solution | 4 |
| Alkylethoxylate | 10 | neat | 1 |
| Citric acid | 2 | in 40 parts water | 0.2 |
| Sodium fluoride | 1 | in 40 parts water | 0.1 |
| Propan-2-ol | 160 | neat | 16 |
| Polyhexamethylenebiguanidine HCld | 80 | as 20% solution | 8 |

In another preferred embodiment, the cleaning preparation is manufactured a super-concentrated preparation by combining the following components as shown in Table V in the order given at ambient temperature. Each component is added successively and stirred gently to give a clear solution before the next component is added. Quantities are in parts by weight.

TABLE V

| Ingredient added | by wt | (active) soln conc | actual wt |
|---|---|---|---|
| Didecyldimethylammonium chloride | 94 | as 50% solution | 188 |
| Alkylbenzyldimethylammonium Chloride | 31 | as 50% solution | 62 |
| Alkylpolyglucoside | 15 | as 50% solution | 30 |
| Alkylethoxylate | 65 | neat | 65 |
| Citric acid | 3 | in 54 parts water | 3 |
| Propan-2-ol | 165 | neat | 165 |
| Polyhexamethylenebiguanidine HCld | 87 | as 20% solution | 433 |
| | | Total wt. | 1000 |

The present invention optimises the activity of quaternary ammonium and biguanidine microbiocides when combinations of non-ionic surfactants and modifiers in aqueous media are present. The present invention demonstrates excellent cleaning properties, including soil lift and suspension, as well as exceptional sporicidal activities.

In a further embodiment of the present invention, the cleaning preparation is manufactured as a super-concentrate which is diluted with water to form a concentrate for transportation to the site of use where it is diluted further with water to prepare the required solution, i.e. for cleaning and/or for rinsing and/or for sanitisation and/or for sterilisation by appropriate dilution.

The present invention thus provides various preparations of differing concentrations, e.g. as a super-concentrate, as a concentrate, as a diluted solution for the manufacture of fabric wipes, as another diluted solution for use as a spray, as a soaking solution of various strengths, as a final rinse aid solution etc.

In one embodiment of the present invention, the preparation comprises an aqueous preparation in terms of weight per percent in the form of wipes having the following components: Propan-2-ol in the amount of 1.65; Didecyldimethylammonium chloride in the amount of 0.94; Polyhexamethylenebiguanidine HCld or polymeric biguanidinnium chloride in the amount of 0.87; Alkylpolyglucoside in the amount of 0.15; Alkylbenzyldimethylammonium chloride in the amount of 0.31; Alkylethoxylate in the amount of 0.65; Citric acid in the amount of 0.03 and Sodium fluoride in the amount of between 0.0001.

In still a further embodiment of the present invention, the preparation comprises an aqueous preparation in terms of weight per percent in the form of a spray having the following components: Propan-2-ol in the amount of 0.66; Didecyldimethylammonium chloride in the amount of 0.38; Polyhexamethylenebiguanidine HCld or polymeric biguanidinnium chloride in the amount of 0.35; Alkylpolyglucoside in the amount of 0.06; Alkylbenzyldimethylammonium chloride in the amount of 0.13; Alkylethoxylate in the amount of 0.26; Citric acid in the amount of 0.012 and Sodium fluoride in the amount of between 0.00004.

In yet a further embodiment of the present invention the cleaning preparation of the present invention may be used for cleaning and/or for sanitising and/or for sterilising. More particularly the preparation of the present invention is used for the enhancement and optimisation in cleaning, sanitising and sterilising. The preparation in accordance with the present invention may be used for the disinfection and sterilisation of materials, commodities and surfaces contaminated with one or more species of micro-organisms including bacteria (and mycobacteria), fungi, algae and yeasts and their associated spores. The preparations may be used in sterilising preparation for killing and rendering spores lifeless and also may affect the necromass so formed in such a way that it becomes easily removable by water rinsing hence reducing the likelihood of biofilm formation.

Furthermore the present invention may be used for cleaning, sanitisation and sterilisation in general and more particularly for cleaning, sanitisation and sterilisation of surfaces as such and equipment used in the human and animal healthcare sector as part of an holistic infection control strategy.

The present invention will now be described in reference to the accompanying examples without being limited by same.

EXAMPLES

Example 1

Example 1 is comprised of a mixture of the biocides: chlorhexidine digluconate and didecyldimethylammonium chloride in the ratio by weight of 1:1 in an aqueous dispersion that included two non-ionic (alcohol ethoxylate and alkylpolyglucoside) surfactants in the proportions by weight of 2:3; the ratio by weight of biocide to non-ionic surfactant was 8:1. A small amount (0.2%) of an organic acid (citric acid) and an aliphatic alcohol (propan-2-ol, 8%) by weight to aid solubility were included.

Example 2

Example 2 is comprised of a mixture of the biocides: polyhexamethylenebiguanidine hydrochloride and didecyldimethylammonium chloride in the ratio by weight of 1:1 in an aqueous dispersion that included two non-ionic (alcohol ethoxylate and alkylpolyglucoside) surfactants in the proportions by weight of 2:3; the ratio by weight of biocide to surfactant was approximately 8:1. A small amount (0.2%) of citric acid was included.

Example 3

Example 3 is comprised of a mixture of the biocides: polyhexamethylenebiguanidine hydrochloride and didecyldimethylammonium chloride in the ratio by weight of 1:1 in an aqueous dispersion that included two non-ionic (alcohol ethoxylate and alkylpolyglucoside) surfactants and a cationic surfactant, e.g. alkylbenzyldimethylammonium chloride, in the proportions by weight of 10:14:3; the ratio by weight of biocide to surfactant was approximately 5.5:1. A small amount (0.2%) of an organic acid and an aliphatic alcohol (16%) by weight to aid solubility were included together with an alkali metal halide salt (0.1%) to modify the viscosity.

The above examples appeared as clear viscous solutions that were diluted with water in the proportions of 1 part example and either 9 or 24 parts of water to provide the solutions subjected to microbiocidal in particular sporicidal evaluation.

Example 4

Microbiological Activity Data

Data were collected following application of standard testing procedures (EN13704) carried out by independent testing laboratories and are shown in Table VI.

TABLE VI

| Example | 1(10%) | 2 (10%) | 3(4%) |
|---|---|---|---|
| Time/min | 5 | 5 | 1 |
| Log reduction | 5.0 | >6.42 | 4.74 |

These and other data indicate a clear advantage to using a combination of non-ionic surfactants and cationic microbiocides to afford effective sporicidal cleaning preparations.

Example 5

Manufacture of Example 3

Super-concentrate solution is manufactured by combining the following components in the order given at ambient temperature, the results are shown in Table VII Each component is added successively and stirred gently to give a clear solution before the next component is added. Quantities are in parts by weight.

TABLE VII

| Ingredient | by wt | soln conc | actual vol added |
|---|---|---|---|
| Didecyldimethylammonium chloride | 100 | as 50% solution | 200 |
| Alkylbenzyldimethylammonium Chloride | 30 | as 50% solution | 60 |
| Alkylpolyglucoside | 40 | as 75% solution | 50 |
| Alkylethoxylate | 10 | neat | 10 |
| Citric acid | 2 | in 40 parts water | 40 |
| Sodium fluoride | 1 | in 40 parts water | 40 |
| Propan-2-ol | 160 | neat | 200 |
| Polyhexamethylenebiguanidine HCld | 80 | as 20% solution | 400 |
| | | Total volume | 1000 |

The sterilising solutions used for the purpose of cleaning, sanitising and sterilising are prepared by appropriate dilution of the above super-concentrate.

Example 6

The microbiocidal efficacy of the diluted aqueous solution for use as a spray based on Example 3 at 4% dilution has been investigated in a series of EN protocols involving contact times of 1 minute with the following spores and organisms and the results are given in Table VIII (the results are given in log reduction).

TABLE VIII

| | | |
|---|---|---|
| Bacillus subtilis spores | 6.23 | |
| Clostridium difficile spores | >6.39 | |
| Pseudomonas aeruginosa | >6.71 | |
| Staphylococcus aureus | >6.50 | |
| Escherichia coli | >6.63 | |
| Enterococcus hirae | >6.42 | |
| Klebsiella pneumoniae | 5.49 | (6.12 with 5 min contact) |
| Enterococcus faecalis | >6.58 | |
| Proteus mirabilis | 5.89 | |
| Streptococcus pyogenes | 5.97 | (>6.16 with 5 min contact) |
| Salmonella choleraesuis | >6.22 | |
| Listeria monocytogenes | >6.33 | |
| Methicillin resistant S. aureus | >6.55 | |
| Mycobacterium terrae | 5.74 | (>6.51 with 3 min contact) |
| HIV | >3.5* | |
| Human Corona Virus | >3.5* | |

TABLE VIII-continued

| | |
|---|---|
| Human Influenza Virus | >4.0 |
| Herpes Simplex Virus | 3.17 |
| Aspergillus niger | 5.68 |
| Candida albicans | 5.83 |
| Tricophyton-mentagrophytes | 4.94 |

Example 7

Example 7 is comprised of a mixture of the biocides: polyhexamethylenebiguanidine hydrochloride and didecyldimethylammonium chloride in the ratio by weight of 1:1.1 in an aqueous dispersion that included two non-ionic (alcohol ethoxylate and alkylpolyglucoside) surfactants and a cationic surfactant, e.g. alkylbenzyldimethylammonium chloride, in the proportions by weight of 4.3:1:2.1; the ratio by weight of biocide to surfactant was approximately 1.63:1. A small amount (0.3%) of an organic acid (citric acid) and an aliphatic alcohol (16.5%) by weight to aid solubility were included.

Example 8

Example 8 is comprised of a mixture of the biocides: polyhexamethylenebiguanidine hydrochloride and didecyldimethylammonium chloride in the ratio by weight of 1:1.1 in an aqueous dispersion that included two non-ionic (alcohol ethoxylate and alkylpolyglucoside) surfactants and a cationic surfactant, e.g. alkylbenzyldimethylammonium chloride, in the proportions by weight of 4.3:1:2.1; the ratio by weight of biocide to surfactant was approximately 1.63:1. A small amount (0.3%) of an organic acid (citric acid) and an aliphatic alcohol (16.5%) by weight to aid solubility were included. Moreover 0.1% sodium fluoride was inserted.

Example 9

Microbiological Activity Data

Data were collected following application of standard testing procedures (EN13704) carried out by independent testing laboratories and are shown in Table IX by checking for the presence of *Bacillus Subtilis*.

TABLE IX

| Example | 7(4%) |
|---|---|
| Time/min | 1 |
| Log reduction | 6.0 |

These and other data indicate a clear advantage to using a combination of surfactants and cationic microbiocides to afford effective sporicidal cleaning preparations.

The invention claimed is:

1. A cleaning preparation comprising an aqueous preparation in terms of weight percent, having the following components: propan-2-ol in the amount of between 0.16 and 30; dodecyldimethylammonium chloride in the amount of between 0.1 and 10; polyhexametylenebiguanidine HCl in the amount of between 0.08 and 9; alkylpolyglucosides in the amount of between 0.04 and 4; alkylbenzyldimethylammonium chloride in the amount of between 0.03 and 4; alkylethoxylate in the amount of between 0.01 and 7; citric acid in the amount of between 0.002 and 0.4; and sodium fluoride in the amount of between 0.0001 and 0.1.

2. A process for manufacture of the cleaning preparation according to claim 1 in which the following steps are carried out:
   a. dissolve the citric acid and sodium fluoride in water;
   b. add the alkylethoxylate and alkylpolyglucoside;
   c. add the didecyldimethylammonium chloride and alkylbenzyldimethylammonium chloride;
   d. add propan-2-ol; and
   e. add polyhexamethylenebiguanidine HCl.

3. The cleaning preparation according to claim 1, which consists in various preparations of differing concentration selected from the group consisting of super-concentrate, concentrate, and diluted solution, wherein the diluted solution is used in applications selected from the group consisting of: a spray of fabric wraps, soaking solutions of various strengths, and a final rinse aid solution.

4. A method for cleaning, sanitising and/or sterilising, the method comprising the application of a cleaning preparation to a surface, the cleaning preparation comprising an aqueous preparation, in terms of weight percent, having the following components: propan-2-ol in the amount of between 0.16 and 30; didecyldimethylammonium chloride in the amount of between 0.1 and 10; polyhexamethylenebiguanidine HCl in the amount of between 0.08 and 9; alkylpolyglucoside in the amount of between 0.04 and 4; alkylbenzyldimethylammonium chloride in the amount of between 0.03 and 4; alkylethoxylate in the amount of between 0.01 and 7; citric acid in the amount of between 0.002 and 0.4; and sodium fluoride in the amount of between 0.0001 and 0.1 wherein the surface is contaminated with one or more species of micro-organisms including selected from the group consisting of: bacteria (and mycobacteria), fungi, algae and yeasts and their associated spores.

5. The cleaning preparation according to claim 1 further comprising fragrances, aromatic and or/coloring materials in the range of 0.1 to 5%.

6. The method of claim 4, for cleaning, sanitization and sterilization of equipment used in human and animal healthcare sector.

7. The method of claim 2, wherein the components are combined at ambient temperature.

* * * * *